(12) United States Patent
Eskuri

(10) Patent No.: US 7,537,600 B2
(45) Date of Patent: May 26, 2009

(54) VALVED EMBOLIC PROTECTION FILTER

(75) Inventor: Alan D. Eskuri, Hanover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 968 days.

(21) Appl. No.: 10/459,746

(22) Filed: Jun. 12, 2003

(65) Prior Publication Data

US 2004/0254601 A1    Dec. 16, 2004

(51) Int. Cl.
*A61M 29/00*    (2006.01)
(52) U.S. Cl. .................................... 606/200
(58) Field of Classification Search ................ 606/200
See application file for complete search history.

(56) References Cited

U.S. PATENT DOCUMENTS

| | | |
|---|---|---|
| 3,472,230 A | 10/1969 | Fogarty |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,494,531 A | 1/1985 | Gianturco |
| 4,590,938 A | 5/1986 | Segura et al. |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,688,553 A | 8/1987 | Metals |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,873,978 A | 10/1989 | Ginsburg |
| 4,921,478 A * | 5/1990 | Solano et al. ............... 604/509 |
| 4,921,484 A | 5/1990 | Hillstead |
| 4,926,858 A | 5/1990 | Gifford, III et al. |
| 4,969,891 A | 11/1990 | Gewertz |
| 4,998,539 A | 3/1991 | Delsanti |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).

(Continued)

*Primary Examiner*—Corrine M McDermott
*Assistant Examiner*—Christopher D Prone
(74) *Attorney, Agent, or Firm*—Crompton Seager & Tufte LLC

(57) ABSTRACT

Embolic protection filters that retain embolic debris captured therein are disclosed. One embodiment of an embolic protection filter includes a filter frame disposable about a guidewire, a filter membrane for filtering embolic debris, and a valve configured to prevent the escape of filtered embolic debris. The valve may comprise a leaflet valve having a plurality of leaflets configured to engage each other about a coaptive region.

10 Claims, 2 Drawing Sheets

U.S. PATENT DOCUMENTS

| | | | |
|---|---|---|---|
| 5,002,560 A | 3/1991 | Machold et al. | |
| 5,011,488 A | 4/1991 | Ginsburg | |
| 5,053,008 A | 10/1991 | Bajaj | |
| 5,071,407 A | 12/1991 | Termin et al. | |
| 5,098,440 A | 3/1992 | Hillstead | |
| 5,100,423 A | 3/1992 | Fearnot | |
| 5,102,415 A | 4/1992 | Guenther et al. | |
| 5,108,419 A | 4/1992 | Reger et al. | |
| 5,133,733 A | 7/1992 | Rasmussen et al. | |
| 5,152,771 A | 10/1992 | Sabbaghian et al. | |
| 5,152,777 A * | 10/1992 | Goldberg et al. | 606/200 |
| 5,160,342 A | 11/1992 | Reger et al. | |
| 5,224,953 A | 7/1993 | Morgentaler | |
| 5,329,942 A | 7/1994 | Gunther et al. | |
| 5,330,484 A | 7/1994 | Gunther | |
| 5,354,310 A | 10/1994 | Garnie et al. | |
| 5,370,657 A | 12/1994 | Irie | |
| 5,375,612 A | 12/1994 | Cottenceau et al. | |
| 5,376,100 A | 12/1994 | Lefebvre | |
| 5,383,887 A | 1/1995 | Nadal | |
| 5,421,832 A | 6/1995 | Lefebvre | |
| 5,423,742 A | 6/1995 | Theron | |
| 5,449,372 A | 9/1995 | Schmaltz et al. | |
| 4,842,579 A | 10/1995 | Shiber | |
| 5,456,667 A | 10/1995 | Ham et al. | |
| 5,462,529 A | 10/1995 | Simpson et al. | |
| 5,536,242 A | 7/1996 | Willard et al. | |
| 5,549,626 A | 8/1996 | Miller et al. | |
| 5,601,595 A | 2/1997 | Smith | |
| 5,626,605 A | 5/1997 | Irie et al. | |
| 5,634,942 A | 6/1997 | Chevillon et al. | |
| 5,658,296 A | 8/1997 | Bates et al. | |
| 5,662,671 A | 9/1997 | Barbut et al. | |
| 5,695,518 A | 12/1997 | Laerum | |
| 5,695,519 A | 12/1997 | Summers et al. | |
| 5,709,704 A | 1/1998 | Nott et al. | |
| 5,720,764 A | 2/1998 | Naderlinger | |
| 5,728,066 A | 3/1998 | Daneshvar | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,795,322 A | 8/1998 | Bouewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,814,065 A * | 9/1998 | Diaz | 606/213 |
| 5,827,237 A * | 10/1998 | Macoviak et al. | 604/246 |
| 5,827,324 A | 10/1998 | Cassell et al. | |
| 5,833,644 A | 11/1998 | Zadno-Azizi et al. | |
| 5,833,650 A | 11/1998 | Imran | |
| 5,833,671 A * | 11/1998 | Macoviak et al. | 604/247 |
| 5,836,868 A | 11/1998 | Ressemann et al. | |
| 5,846,251 A * | 12/1998 | Hart | 606/127 |
| 5,846,260 A | 12/1998 | Maahs | |
| 5,848,964 A | 12/1998 | Samuels | |
| 5,876,367 A | 3/1999 | Kaganov et al. | |
| 5,895,399 A | 4/1999 | Barbut et al. | |
| 5,910,154 A | 6/1999 | Tsugita et al. | |
| 5,911,734 A | 6/1999 | Tsugita et al. | |
| 5,925,016 A | 7/1999 | Chornenky et al. | |
| 5,925,060 A | 7/1999 | Forber | |
| 5,925,062 A | 7/1999 | Purdy | |
| 5,935,139 A | 8/1999 | Bates | |
| 5,938,683 A | 8/1999 | Lefebvre | |
| 5,941,869 A | 8/1999 | Patterson et al. | |
| 5,941,896 A | 8/1999 | Kerr | |
| 5,947,995 A | 9/1999 | Samuels | |
| 5,954,745 A | 9/1999 | Gertler et al. | |
| 5,968,071 A | 10/1999 | Chevillon et al. | |
| 5,980,555 A | 11/1999 | Barbut et al. | |
| 5,984,947 A | 11/1999 | Smith | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,757 A * | 5/2000 | Macoviak et al. | 604/247 |
| 6,059,814 A | 5/2000 | Ladd | |
| 6,066,149 A | 5/2000 | Samson et al. | |
| 6,066,158 A | 5/2000 | Engelson et al. | |
| 6,068,645 A | 5/2000 | Tu | |
| 6,086,577 A * | 7/2000 | Ken et al. | 606/1 |
| 6,086,605 A | 7/2000 | Barbut et al. | |
| 6,117,154 A | 9/2000 | Barbut et al. | |
| 6,129,739 A | 10/2000 | Khosravi | |
| 6,136,016 A | 10/2000 | Barbut et al. | |
| 6,142,987 A | 11/2000 | Tsugita | |
| 6,152,946 A | 11/2000 | Broome et al. | |
| 6,165,200 A * | 12/2000 | Tsugita et al. | 606/200 |
| 6,168,579 B1 | 1/2001 | Tsugita | |
| 6,171,327 B1 | 1/2001 | Daniel et al. | |
| 6,171,328 B1 | 1/2001 | Addis | |
| 6,179,851 B1 | 1/2001 | Barbut et al. | |
| 6,179,859 B1 * | 1/2001 | Bates et al. | 606/200 |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,325,815 B1 | 12/2001 | Kusleika et al. | |
| 6,336,934 B1 | 1/2002 | Gilson et al. | |
| 6,344,049 B1 | 2/2002 | Levinson et al. | |
| 6,361,545 B1 * | 3/2002 | Macoviak et al. | 606/200 |
| 6,364,895 B1 | 4/2002 | Greenhalgh | |
| 6,375,670 B1 | 4/2002 | Greenhalgh | |
| 6,383,206 B1 | 5/2002 | Gillick et al. | |
| 6,391,044 B1 | 5/2002 | Yadav et al. | |
| 6,398,756 B2 | 6/2002 | Peterson et al. | |
| 6,413,235 B1 | 7/2002 | Parodi | |
| 6,432,122 B1 | 8/2002 | Gilson et al. | |
| 6,443,926 B1 | 9/2002 | Kletschka | |
| 6,485,502 B2 | 11/2002 | Michael et al. | |
| 6,494,895 B2 | 12/2002 | Addis | |
| 6,506,205 B2 | 1/2003 | Goldberg et al. | |
| 6,511,496 B1 | 1/2003 | Huter et al. | |
| 6,540,722 B1 | 4/2003 | Boyle et al. | |

| | | | |
|---|---|---|---|
| 6,540,768 B1 | 4/2003 | Diaz et al. | |
| 6,544,280 B1 | 4/2003 | Daniel et al. | |
| 6,554,849 B1 | 4/2003 | Jones et al. | |
| 6,558,405 B1 | 5/2003 | McInnes | |
| 6,565,591 B2 | 5/2003 | Brady et al. | |
| 6,575,996 B1 | 6/2003 | Denison et al. | |
| 2002/0161390 A1* | 10/2002 | Mouw | 606/200 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |
| WO | WO 02/094111 A2 | 11/2002 |

OTHER PUBLICATIONS

"Endovascular Grafts, Stents Drive Interventional Radiology Growth," *Cardiovascular Device Update*, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," *AJR*, 141:601-604 (Sep. 1983).
Cragg, Andrew et al., "Nonsurgical Placement of Arterial Endoprosthesis: A New Technique Using Nitinol Wire," AJR, pp. 261-263 (Apr. 1983).
Diethrich et al., "Percutaneous Techniques for Endoluminal Carotid Interventions," *J. Endovasc. Surg.*, 3:182-202 (1996).
Fadali, A. Moneim, "A filtering device for the prevention of particulate embolization during the course of cardiac surgery," Surgery, 64(3):634-639 (Sep. 1968).
Haissaguerre et al., "Spontaneous Initiation of Atrial Fibrillation by Ectopic Beats Originating in the Pulmonary Veins," *The New England Journal of Medicine*, 339(10):659-666 (Sep. 1988).
Jordan, Jr. et al., "Microemboli Detected by Transcranial Doppler Monitoring . . . ," Cardiovascular Surgery, 7(1)33-38 (Jan. 1999).
Lesh, "Can Catheter Ablation Cure Atrial Fibrillation?" *ACC Current Journal Review*, pp. 38-40 (Sep./Oct. 1997).
Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," Catheterization and Cardiovascular Diagnosis, 31:17-84 (1994).

Moussa, MD, Issaam "Stents Don't Require Systemic Anticoagulation . . . But the Technique (and Results) Must be Optimal," Journal of Invasive Cardiol., 8(E):3E-7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," Cardiovascular & Interventional Radiology, 21(5):386-392 (1998).

Theron et al., "New Triple Coaxial Catheter System for Carotid Angioplasty with Cerebral Protection," American Journal of Neuroradiology, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," American Heart Journal, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

VALVED EMBOLIC PROTECTION FILTER

FIELD OF THE INVENTION

The present invention relates generally to the field of embolic protection devices. More specifically, the present invention relates to valved embolic protection filters insertable within a blood vessel.

BACKGROUND OF THE INVENTION

Intravascular devices such as embolic protection filters are generally placed in a body lumen such as an artery or vein, downstream of a therapeutic site to filter emboli contained in the blood. In a typical procedure such as percutaneous transluminal coronary angioplasty (PTCA), an embolic protection filter is loaded into a delivery device such as a catheter or sheath, and advanced along a guidewire in a collapsed position to a location downstream a lesion. Once positioned downstream the lesion, the embolic protection filter is ejected from the delivery device and deployed in the blood vessel. An angioplasty catheter containing an angioplasty balloon is then advanced along the guidewire and positioned across the site of the lesion to be dilated. The angioplasty balloon is then inflated, forcing the lesion to rupture and dislodge from the wall of the vessel. The dislodged debris is then carried downstream towards the embolic protection filter, where it can be collected and stored for later removal.

A number of embolic protection filters have been developed to filter embolic debris contained in the blood stream. Typically, these devices contain a support structure coupled to a filter membrane that filters contaminants in the blood stream. The support structure generally includes a number of wires, ribs, or struts forming a filter frame that supports the filter membrane in an expanded position within the vessel. As the embolic debris passes through the mouth of the filter, it is deposited along the inner wall of the filter membrane, typically at a location distal the mouth of the filter at or near the apex of the filter. At the conclusion of the therapeutic procedure, the filter frame is then collapsed within a retrieval catheter and removed from the vessel.

As the filter frame is collapsed, the generally laminar flow of blood in the vessel may be temporarily disturbed, resulting in a turbulence spot at or near the mouth of the filter. A slight backpressure may result, causing the captured embolic debris to flow upstream towards the mouth of the filter. In some situations, the amount of embolic debris collected in the filter membrane may affect the downstream perfusion of blood through the filter, drawing the embolic debris proximally towards the mouth of the filter. As a result, some of the filtered embolus may escape from the filter and reenter the blood stream.

SUMMARY OF THE INVENTION

The present invention relates to valved embolic protection filters insertable within a blood vessel. An embolic protection filter in accordance with an exemplary embodiment of the present invention may include a filter frame disposable about an elongated member, a filter membrane coupled to the filter frame for filtering embolic debris, and a valve configured to prevent backflow of embolic debris captured within the filter membrane.

The valve may comprise a plurality of coaptive leaflets configured to engage each other about a coaptive region, occluding the mouth or opening of the filter. The leaflets may be pivotally mounted about an annular-shaped member defined by the filter frame, and may be inwardly radially sloped in the distal direction, forming a generally conical shaped or duckbill configuration that provides a seal about the outer periphery of the guidewire.

The leaflets are formed of a relatively elastic material having sufficient resiliency to bend from a nominally closed position to an open position when subjected to the downstream flow of blood within the vessel. The leaflets may form an aperture configured to slidably receive the guidewire therethrough. The aperture may have a cross-sectional dimension slightly larger than the outer diameter of the guidewire. Alternatively, the aperture may have cross-sectional dimension smaller than the outer diameter of the guidewire, but the leaflets may be of sufficient resilience to permit an elastic expansion of the aperture to accommodate the guidewire therethrough.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
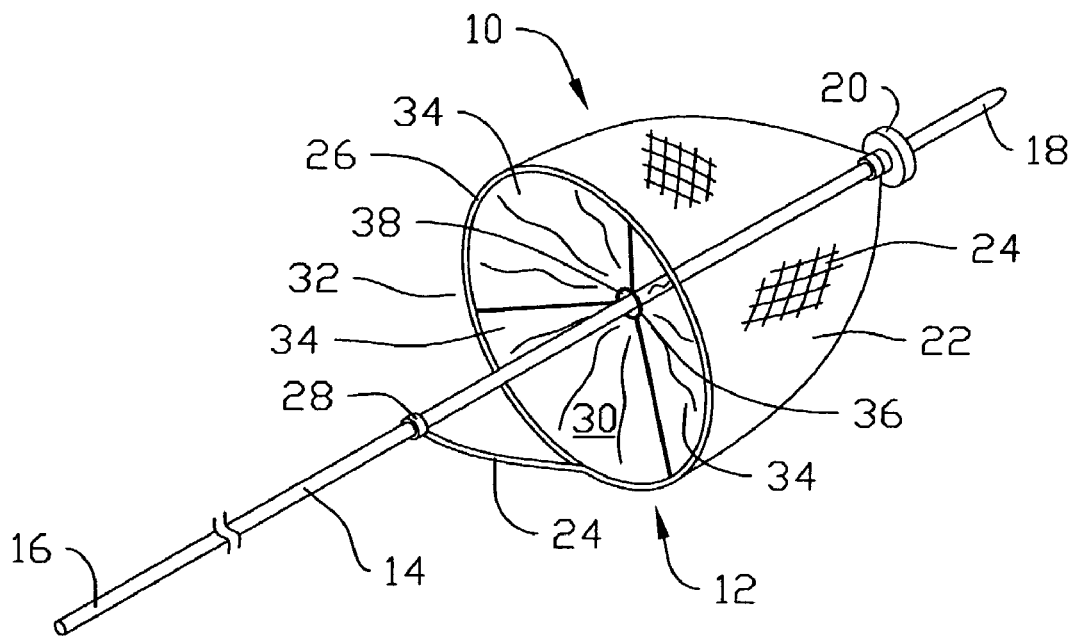
FIG. 1 is a perspective view of a valved embolic protection filter in accordance with an exemplary embodiment of the present invention, showing the filter in an expanded position.

FIG. 1 is a perspective view of a valved embolic protection filter 10 in accordance with an exemplary embodiment of the present invention. As shown in an expanded position in FIG. 1, embolic protection filter 10 includes a filter frame 12 slidably and rotationally disposed about an elongated member such as a guidewire 14. Guidewire 14 has a proximal end 16, a distal end 18, and a distal stop 20. The distal stop 20 is configured to prevent the user from advancing the embolic protection filter 10 beyond the distal end 18 of the guidewire during placement of the device in a blood vessel.

A filter membrane 22 attached to the filter frame 12 is adapted to collect and store embolic debris dislodged during a therapeutic procedure such as percutaneous transluminal coronary angioplasty (PTCA). The filter membrane 22 may comprise a microporous membrane or mesh screen having a number of openings or pores 24 adapted to filter embolic debris flowing through the filter 10. The filter membrane 22 may be formed of a polymeric material such as polypropylene (PP), polyvinylchloride (PVC), polyamide (nylon), polyurethane, polyester, polyethylene tetraphalate, polyether-ether ketone (PEEK), polyether block amide (PEBA), polytetraflouroethylene (PTFE), or any mixture, blend or combination thereof. Alternatively, or in addition, the filter membrane 22 may be formed of a metal or metal alloy such as stainless steel, nickel-titanium (Nitinol), or platinum.

In certain embodiments, embolic protection filter 10 may include an anti-inflammatory agent to reduce damage to the patient's vascular tract caused during therapeutic the procedure. Examples of such anti-inflammatory agents include dexamethasone, prednisolone, corticosterone, budesonide, estrogen, sulfasalazine, mesalamine, or any suitable combination or mixture thereof. The embolic protection filter 10 may also contain an anti-thrombogenic coating to prevent the formation of clots within the vasculature. Examples of suitable anti-thrombogenic coatings include heparin (and derivatives thereof), urokinase, and dextrophenylalanine proline arginine chloromethylketone.

The filter frame 12 may include one or more struts 24, and an annular-shaped member 26. The one or more struts 24 and annular-shaped member 26 may be formed from a single strand of wire, or as separate elements attached together by solder, weld, adhesion or other suitable bonding technique. The one or more struts 24 may be attached to a tubular segment 28 having an inner lumen configured to slidably receive the guidewire 14, allowing the user to move the filter 10 along the guidewire 14. Alternatively, the one or more struts 24 can be coupled directly to the guidewire 14, fixedly securing the filter 10 to the guidewire 14.

The annular-shaped member 26 serves the dual purpose of supporting and expanding the filter membrane 22 within the blood vessel, and as a valve body annulus for a valve 30 that prevents backflow of embolic debris collected within the filter membrane 22. The annular-shaped member 26 may be biased to radially open when placed in the blood vessel, forming a proximal mouth or opening 32 for the filter membrane 22. As the embolic debris enters the proximal mouth or opening 32 of the filter 10, it passes through the valve 30 and into the filter membrane 22, where it is collected and stored for later removal.

In the exemplary embodiment illustrated in FIG. 1, valve 30 comprises a plurality of coaptive leaflets 34 configured to engage each other at a coaptive region 36 about the outer periphery of the guidewire 14. In use, the leaflets 34 cooperate in a manner to permit passage of blood through the filter 10, but prevent the escape of filtered embolic debris through the proximal mouth or opening 32 of the filter 10.

The coaptive region 36 forms an aperture 38 configured to slidably receive the guidewire 14. The aperture 38 may be located in the central portion of the annular-shaped member 24, and may be sized to slidably receive the guidewire 14 therethrough. In certain embodiments, for example, the aperture 38 may have a cross-sectional dimension slightly larger than the outer diameter of the guidewire 14. In other embodiments, the aperture 38 may have a cross-sectional dimension smaller than the outer diameter of the guidewire 14, but the leaflets 34 may have sufficient resilience to permit an elastic expansion of the aperture 38 to accommodate the guidewire 14 therethrough. In one exemplary embodiment, the aperture 38 may have a diameter of about 0.018 inches, corresponding to the size of many conventional guidewires used in the field of embolic protection.

Figure 2:
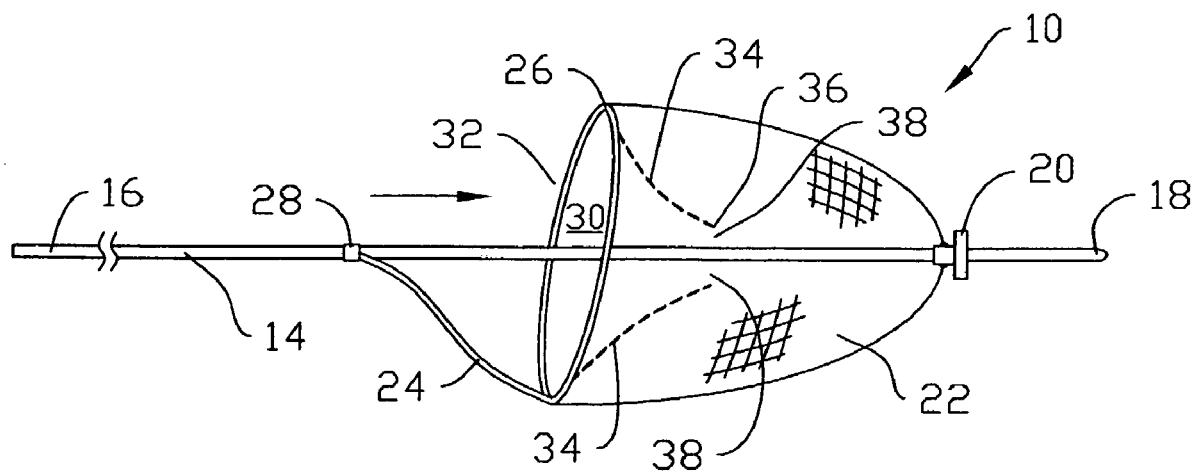
FIG. 2 is a side view of the valved embolic protection filter of FIG. 1, showing the leaflets deflected away from the coaptive region in an open position.

Referring now to FIG. 2, it can be further seen that the coaptive leaflets 34 are pivotally mounted to the annular-shaped member 26, and are formed of an elastomeric material having sufficient resiliency to bend in response to the downstream flow of blood. As indicated by the arrow in FIG. 2, the kinetic energy resulting from the flow of blood in the downstream direction causes the leaflets 34 to deflect away from the coaptive region 36 and open slightly, allowing the contaminated blood to enter the filter membrane 22. As the flow of blood is disrupted (e.g. during filter retrieval) the leaflets 34 resiliently return to their nominally closed position about the coaptive region 36, occluding the proximal mouth or opening 32 of the filter 10 and preventing the backflow of contaminants into the bloodstream. The valve 30 may be inwardly radially sloped in the distal direction, forming a generally conical shaped configuration that provides a seal about the outer periphery of the guidewire 14 when the leaflets 34 are in the closed position.

The leaflets 34 may be formed of any number of biocompatible materials such as silicone rubber, thermoplastic rubber, thermoset rubber, polyurethane, thermoset polyurethane (TPU), polyethylene (PE), polytetraflouroethylene (PTFE), or any mixture, blend or combination thereof. The leaflets 34 may be constructed from a relatively resilient material biased to return to a nominally closed position about the coaptive region 36. The leaflets 34 may be formed integrally with the annular-shaped member 26, or can be formed as separate elements and attached together.

Figure 3:
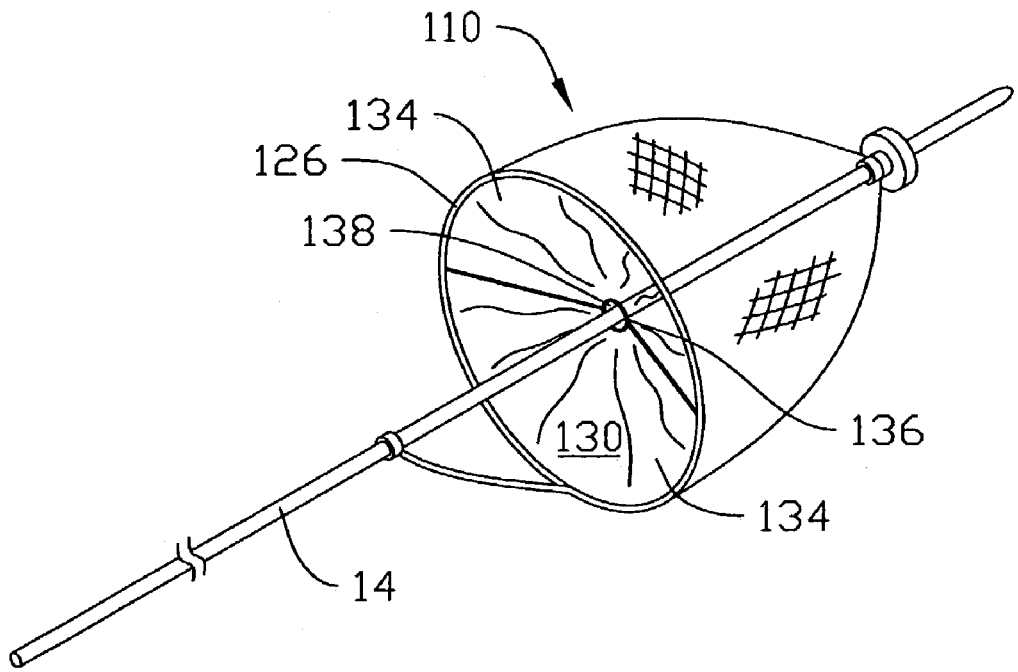
FIG. 3 is a perspective view of a valved embolic protection filter in accordance with another exemplary embodiment of the present invention, wherein the filter includes two coaptive leaflets.

Although the exemplary embodiment illustrated in FIGS. 1-2 includes a valve 30 having three coaptive leaflets 34, it should be understood that any number or configuration of leaflets can be used in accordance with the present invention. For example, as shown in FIG. 3, an embolic protection filter 110 in accordance with an embodiment of the present invention may include a bi-leaflet valve 130 comprising two oppositely disposed leaflets 134 pivotally mounted about the annular-shaped member 126, forming a split coaptive region 136 about the outer periphery of the guidewire 14.

Figure 4:
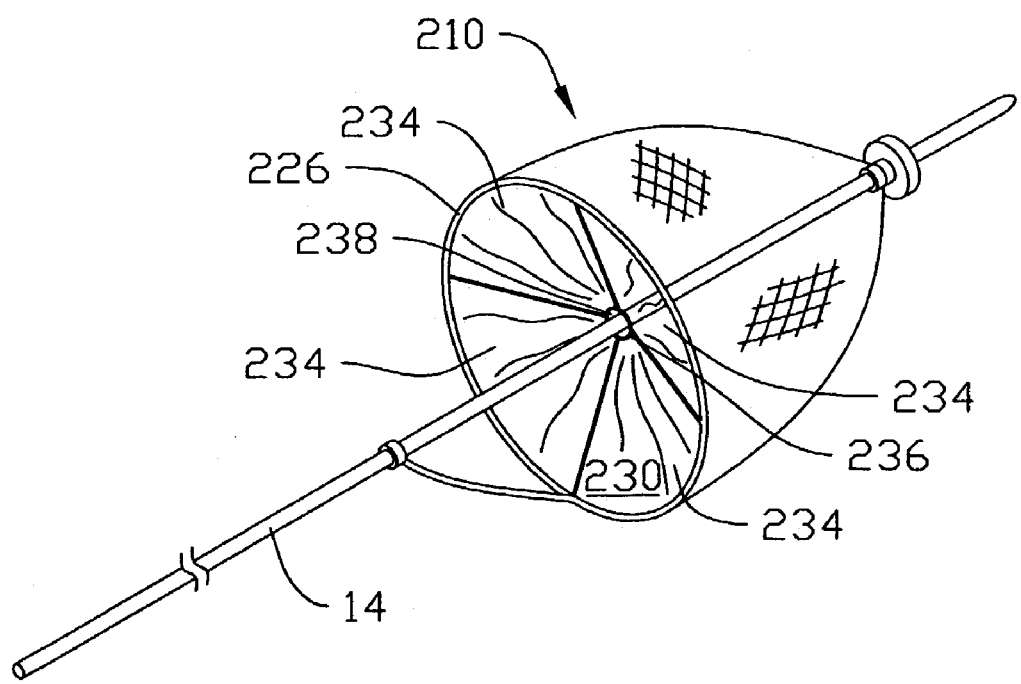
FIG. 4 is a perspective view of a valved embolic protection filter in accordance with yet another exemplary embodiment of the present invention, wherein the filter includes four coaptive leaflets.

As with other embodiments described herein, the two leaflets 134 may be inclined radially inwardly in the distal direction forming a duck-billed configuration. In yet another exemplary embodiment illustrated in FIG. 4, an embolic protection filter 210 may be equipped with a leaflet valve 230 having four coaptive leaflets 234 pivotally mounted about the annular-shaped ring 226, forming a coaptive region 236 about the outer periphery of the guidewire 14.

The selection and construction of a particular valve depends on several design factors, including the size of the annular-shaped member and filter membrane, the types of material used in the formation of the leaflets, and the amount of force desired to open the leaflets. While the filters described and illustrated herein are generally referred to as basket-type filters, it should be understood that the present invention is not limited to such filter types. A valved embolic protection filter in accordance with the present invention may comprise any number of filter designs having a filter membrane or other filtering structure that collects and stores embolic debris.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. An embolic protection filter, comprising:
a filter frame including an annular-shaped member disposable about an elongated member;

a filter membrane coupled to said annular-shaped member, said filter membrane comprising a microporous membrane or mesh screen for filtering embolic debris within a blood vessel; and a plurality of coaptive leaflets pivotally mounted to the annular-shaped member, said plurality of coaptive leaflets configured to engage each other about a coaptive region forming an aperture configured to receive the elongated member.

2. The embolic protection filter of claim 1, wherein said elongated member is a guidewire.

3. The embolic protection filter of claim 1, wherein said annular-shaped member forms a proximal mouth or opening for the filter membrane.

4. The embolic protection filter of claim 1, wherein said annular-shaped member is biased to radially expand and deploy the filter membrane when placed in the blood vessel.

5. The embolic protection filter of claim 1, wherein said plurality of leaflets are configured to deflect away from the coaptive region in response to the flow of blood in the downstream direction, and resiliently return to the coaptive region in response to the flow of blood in the upstream direction.

6. The embolic protection filter of claim 1, wherein said plurality of leaflets are inclined radially inwardly in a distal direction.

7. The embolic protection filter of claim 1, wherein said plurality of leaflets are formed of an elastomeric material.

8. The embolic protection filter of claim 7, wherein said elastomeric material is selected from the group consisting of silicone rubber, thermoplastic rubber, thermoset rubber, polyurethane, thermoset polyurethane, polyethylene, and polytetraflouroethylene.

9. The embolic protection filter of claim 1, wherein said plurality of leaflets comprise two leaflets.

10. An embolic protection filter, comprising:

a filter frame including an annular-shaped member disposable about an elongated member;

a filter membrane coupled to said annular-shaped member, said filter membrane comprising a microporous membrane or mesh screen for filtering embolic debris within a blood vessel; and a plurality of coaptive leaflets pivotally mounted to the annular-shaped member, said plurality of coaptive leaflets configured to engage each other about a coaptive region forming an aperture configured to receive the elongated member;

wherein said plurality of leaflets are configured to deflect away from the coaptive region in response to the flow of blood in the downstream direction, and resiliently return to the coaptive region in response to the flow of blood in the upstream direction.

* * * * *